United States Patent [19]

Namekawa et al.

[11] Patent Number: 4,651,742

[45] Date of Patent: Mar. 24, 1987

[54] ULTRASONIC DOPPLER DIAGNOSTIC DEVICE

[75] Inventors: Kouroku Namekawa; Akimitsu Harada, both of Tokyo, Japan

[73] Assignee: Aloka Co., Ltd., Tokyo, Japan

[21] Appl. No.: 717,495

[22] Filed: Mar. 28, 1985

[30] Foreign Application Priority Data

Apr. 2, 1984 [JP] Japan .................................. 59-063282

[51] Int. Cl.[4] ............................................. A61B 10/00
[52] U.S. Cl. .................................. 128/663; 73/861.25
[58] Field of Search ................................. 128/660-663; 73/861.25, 631

[56] References Cited

U.S. PATENT DOCUMENTS 4,145,741  3/1979  Nappin ............................. 73/631 X
4,289,140  9/1981  Carpenter et al. ................ 73/631 X
4,543,826  10/1985  Ferrari ............................ 128/660 X

OTHER PUBLICATIONS

Baker, D. W., "Pulsed Ultrasonic Doppler Blood Flow Sensing" IEEE Transactions on Sonics & Ultrasonics, vol. Su-17, No. 3, Jul. 1970.

Primary Examiner—Kyle L. Howell
Assistant Examiner—Francis J. Jaworski
Attorney, Agent, or Firm—Koda and Androlia

[57] ABSTRACT

An ultrasonic diagnostic device for measuring the velocity of blood flow within a living body comprises a receiver for amplifying a received wave in accordance with a logarithmic amplification characteristic and at least one inverse logarithmic converter which produces an output having an inverse logarithmic characteristic with respect to the input thereto. As a result, the device can carry out high-precision measurement of blood flow even when the component of the received wave corresponding to the blood flow is much smaller than a component of the received wave corresponding to the wall of the blood vessel or heart through which the blood is flowing.

1 Claim, 5 Drawing Figures

A

B

C

ULTRASONIC DOPPLER DIAGNOSTIC DEVICE

BACKGROUND OF THE INVENTION

1. Field of the Invention

This invention relates to an ultrasonic Doppler diagnostic device, more particularly to an improved ultrasonic Doppler diagnostic device for detecting blood flow within a living organism or for measuring the velocity or the amount of such blood flow.

2. Description of the Prior Art

The ultrasonic Doppler method is widely used for noninvasively detecting and measuring the movement of a moving member within a living organism and, specifically, is commonly used for noninvasive detection and measurement of blood flow within the heart, blood vessels etc.

Generally speaking, however, the ultrasonic wave reflected from the blood flow is mixed together with an ultrasonic wave component reflected by the wall of the blood vessel or the heart which surrounds the blood flow (such component being referred to as the "wall signal" hereinafter). This is particularly troublesome since the the blood flow signal is much weaker than the wall signal.

Although the amplitude of the wall signal can be reduced by focusing the ultrasonic wave into a fine beam, there is a limit to how sharply the beam can be focused so that even when this method is used the reflected wave nevertheless includes a high-level wall signal along with a low-level blood flow signal. As a result, there has been the disadvantage that the strong wall signal makes it difficult to obtain the desired blood flow signal.

Conventionally, the separation of the blood flow signal from the wall signal has been carried out on the basis of frequency difference. This is possible since the wall signal is a wave reflected from a substantially nonmoving portion so that its frequency following comparison with the reference wave according to the Doppler method is relatively low, whereas the corresponding frequency for the wave reflected from the moving blood is, because of the Doppler effect, relatively high. This frequency difference can be used to separate the two signals. More specifically, by passing the mixed signals through a filter, the strong but low frequency wall signal can be separated from the weaker, higher frequency blood flow signal.

Nevertheless, conventional devices operating on this principle have not been able to produce the desired results when the detection or measurement is carried out for blood flow within very fine blood vessels. This is because in such cases the ratio of the wall signal to the blood flow signal becomes extremely large so that when the blood flow signal is amplified by a degree adequate to make it detectable, the wall signal, which is amplified by the same degree, becomes so large as to saturate the receiver circuit. As a consequence, it becomes difficult, if not impossible, to detect the blood flow signal.

SUMMARY OF THE INVENTION

In view of the above-mentioned disadvantages inherent in conventional apparatuses, it is the object of the present invention to provide an improved ultrasonic Doppler diagnostic device which can effectively detect blood flow within fine blood vessels or in regions near the heart wall.

In order to attain this object, the present invention provides an ultrasonic Doppler diagnostic device for detecting or measuring blood flow by use of the Doppler effect, said ultrasonic Doppler diagnostic device comprising means for amplifying a received signal in accordance with a logarithmic characteristic, and then reconverting the received signal amplified in such manner in accordance with an inverted logarithmic characteristic.

DESCRIPTION OF THE PREFERRED EMBODIMENT

Figure 1:
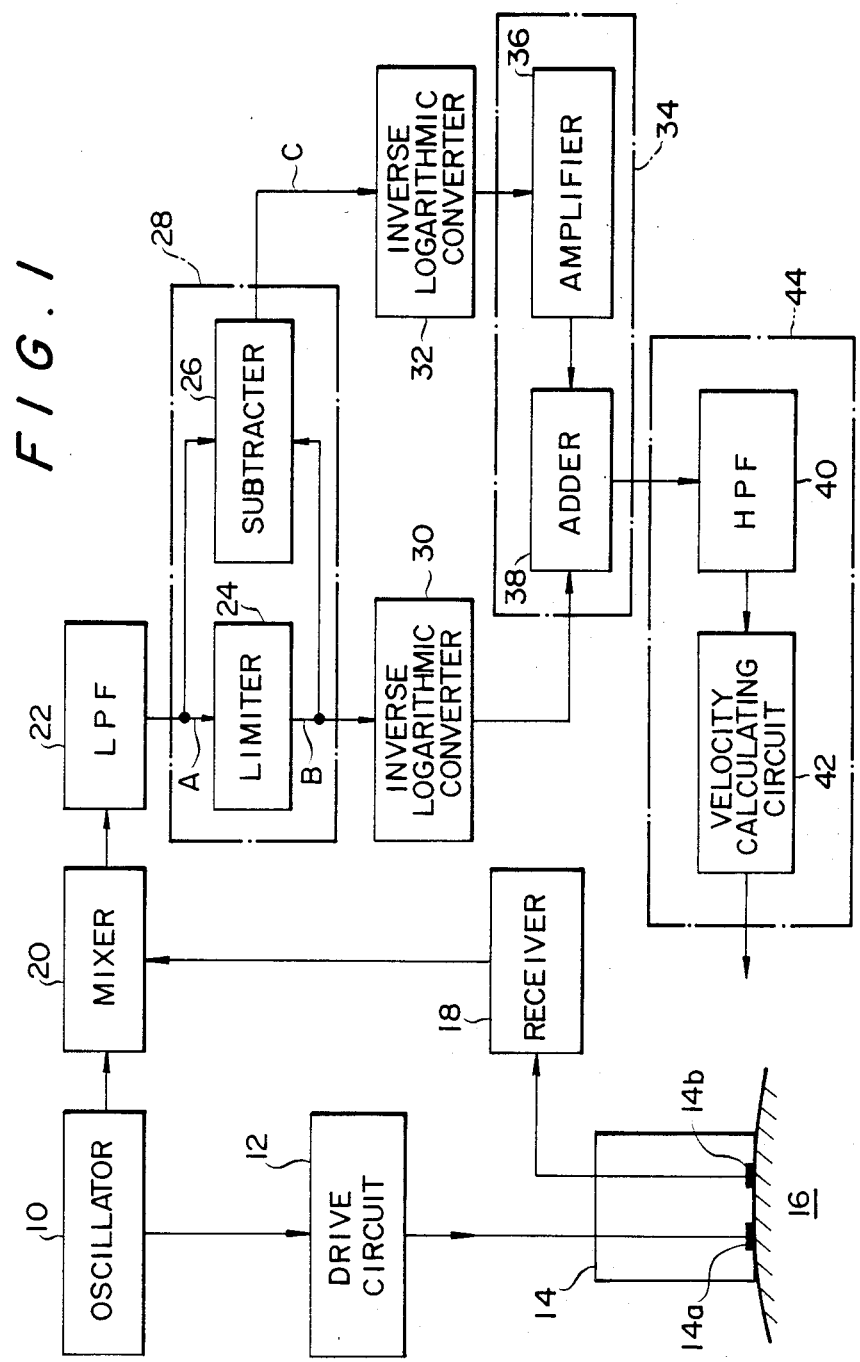
FIG. 1 is a block circuit diagram of one embodiment of the ultrasonic Doppler diagnostic device according to the invention.

Referring to FIG. 1, an oscillator 10 produces a stable high frequency signal which is passed through a drive circuit 12 and used to drive a piezoelectric transmitter element 14a of a probe 14. As a result, an ultrasonic wave is radiated from the piezoelectric transmitter element 14a toward a living organism 16 and upon entering the organism 16 is partially reflected. The reflected wave is picked up by a piezoelectric receiver element 14b provided in the probe 14 and is converted into an electric signal.

The electric signal produced from the reflected wave is amplified by a receiver 18, which in accordance with one feature of the present invention carries out logarithmic amplification.

For the reason mentioned earlier, the electric signal received by the receiver 18 from the piezoelectric receiver element 14b includes a large wall signal of high output level together with a weak blood flow signal. If this composite signal should be amplified by an amplifier with an ordinary amplification characteristic, the amplifier would reach saturation because of the large ratio between the wall signal and the blood flow signal. As a result, it would be difficult to detect the weak blood flow signal. Moreover, this difficulty would increase in proportion to decreasing size of the blood vessel since the smaller is the blood vessel, the greater is the disparity between the strengths of the wall signal and the blood flow signal.

Therefore, as stated above, in the present invention the receiver 18 is designed to amplify according to a logarithmic amplification characteristic so as to prevent saturation and make it possible to detect the weak blood flow signal.

The receiver 18 can be easily constituted to exhibit a logarithmic amplification characteristic by using a conventional logarithmic amplifier, an amplifier provided with an automatic gain control circuit, or the like.

The output from the receiver 18 is supplied to a mixer 20 which also receives the signal output by the oscillator 10. The two signals are mixed and detected in the mixer 20, with the signal from the oscillator 10 being used as the reference signal.

The output from the mixer is forwarded to a low-pass filter 22 which passes only the difference frequency obtained by mixing the two frequencies in the mixer 20 so that the output from the low-pass filter constitutes a frequency shift signal resulting from the comparison of the two signals. It must be noted, however, that this frequency shift signal includes both a large, low-frequency signal component attributable to the slow movement of the blood vessel wall, heart wall etc. and a small, high-frequency blood flow signal component attributable to the blood flow. It is of course necessary to separate out the blood flow signal component.

Although this separation can be carried out by use of a high-pass filter, the method used in the present invention takes advantage of the fact that, as was explained above, the received signal is subjected to logarithmic amplification. As a result, in amplifying the mixed signal consisting of the wall signal (a strong signal) and the blood flow signal (a weak signal) there is no danger of the receiver being saturated by the strong signal. On the other hand, however, there is the problem that the reception gain with respect to the weak signal is extremely low.

As it is difficult to detect the blood flow signal from this low level signal, the present invention compensates for the aforesaid logarithmic amplification by a reconversion conducted by inverse logarithmic converters exhibiting inverse logarithmic conversion characteristics which are the reverse of the logarithmic amplification characteristic of the receiver 18. Therefore, by the employment of this inverse logarithmic conversion there can be realized an overall compensation for the logarithmic amplification by the receiver 18 so that there can be obtained an amplified signal substantially identical to that which would be obtained by linear amplification, meaning that there can be realized an overall gain of a specific fixed level which is large enough to enable reliable detection of the blood flow signal regardless of the level of the strong signal.

As the inverse logarithmic coverters it is possible to use amplifiers having a feedback circuit having a logarithmic feedback characteristic or to use a conventional antilog circuit. It should be noted, however, that the antilog circuit is suitable only within a relatively narrow operational range in view of the fact that it is operationally restricted to within the range of linear output.

One feature of the illustrated embodiment is that it is designed to expand the output operational range of the antilog circuit thus overcoming the aforementioned drawback. This expansion of range is achieved by amplitude splitting.

More specifically, the output from the low-pass filter 22 is applied to an amplitude splitter 28 constituted by a limiter 24 and a subtracter 26. With this arrangement, the input amplitude is effectively limited by the limiter 24.

Figure 2:
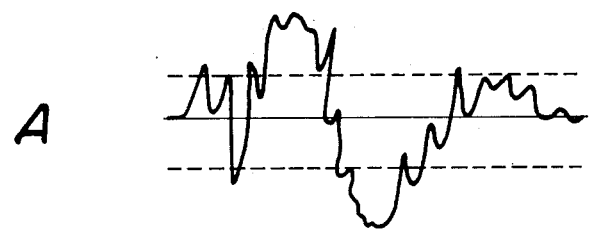
FIGS. 2A through 2C are waveform diagrams for illustrating the amplitude splitting operation of the device shown in FIG. 1.
Figure 2:
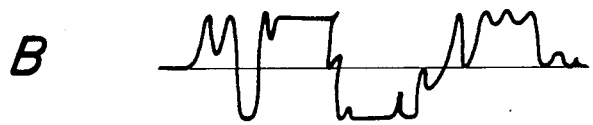
Figure 2:

FIG. 2A shows the waveform input to the amplitude splitter 28 from the low-pass filter 22, while FIG. 2B shows the waveform output by the limiter 24. It will be noted that the output wave is sliced at both the top and the bottom.

The difference between the input to and output from the limiter 24 is calculated by the subtracter 26, which produces an output of the waveform shown in FIG. 2C. From this it will be understood that the amplitude splitter 28 divides the input wave A into two output waves B and C.

The outputs B and C from the limiter 24 and the subtracter 26 are respectively sent to inverse logarithmic converters 30 and 32. By these converters, which constitute one of the characterizing features of this invention, the inputs from the limiter 24 and the subtracter 26 are converted in accordance with an inverse logarithmic characteristic.

As was mentioned earlier, the inverse logarithmic converters 30, 32 can be easily constituted as amplifiers having feedbacks employing circuits exhibiting an inverse logarithmic characteristic.

Figure 3:
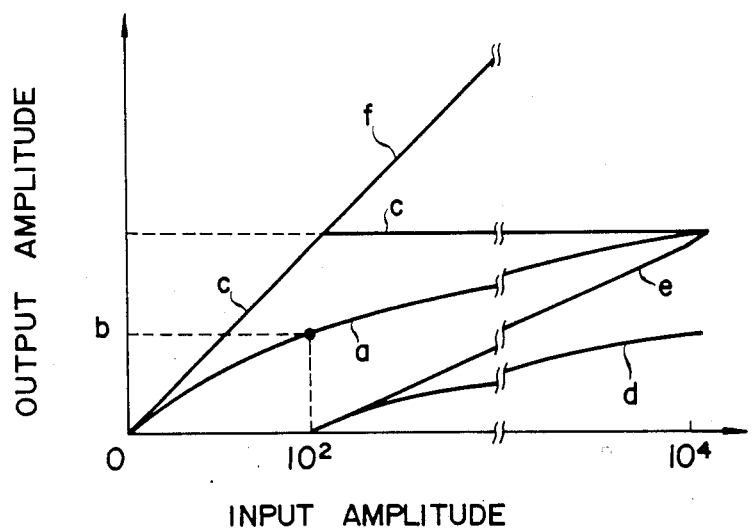
FIG. 3 is a graph showing the characteristics of logarithmic and inverted logarithmic conversion in the embodiment shown in FIG. 1.

In FIG. 3 are shown characteristic curves representing the relationship between input amplitude and output amplitude in the embodiment shown in FIG. 1. In the figure, input amplitude is represented on the x-axis and output amplitude on the y-axis.

The curve a in FIG. 3 shows the input-output characteristic of the receiver section constituted by the receiver 18 and the low-pass filter 22, the output of which is input to the amplitude splitter 28. The curve a is split in two by the amplitude splitter 28 and the low amplitude side thereof, that is the part in the region between 0 and b, is subjected to inverse logarithmic conversion by the inverse logarithmic converter 30 so as to realize an overall amplification characteristic as shown by the broken line c. As shown in the figure, a linear conversion characteristic is obtained within the range of 100 times the input. Therefore, even in the case of a relatively small input, the output signal within this low amplitude region is utilizable.

In the case of a large input, on the other hand, in order to prevent the output from becoming excessively large, the present embodiment is provided with an additional inverse logarithmic converter 32 to which the subtracter 26 supplies the signal waveform C, namely a signal waveform corresponding to the part sliced off by the limiter 24. As a result, in the region of the corresponding input curve d there is attained a linear characteristic as shown by the curve e.

It is clear, of course, that the inclination of the straight line e is 1/100 that of the curve c.

As is clear from the foregoing, in the present embodiment, the two outputs from the amplitude splitter 28 are separately converted so as to exhibit linear characteristics, making it possible to carry out detection with respect to a wide range of input signals.

Moreover, as the outputs from the two converters 30, 32 in this embodiment have different weights, these outputs are further applied to a weighting adder 34 so as to adjust their respective weights.

In the illustrated embodiment, the weighting adder is constituted of an amplifier 36 for amplifying the output from the inverse logarithmic converter 32 and an adder 38 for adding the output from the amplifier 36 to the output from the inverse logarithmic converter 30. In this particular embodiment, the gain of the amplifier 36 is set at 100 so that the aforesaid curves c and d are adjusted to the same level.

As a consequence, the adder 38 is able to add the two signals produced by the amplitude splitting operation under the same conditions. The resulting output is shown in FIG. 3 by the characteristic curve f on the high amplitude side.

The output from the weighting adder 34 is forwarded to a high-pass filter 40 which, as mentioned earlier, removes the low-frequency component corresponding to the movement of the wall of the blood vessel or heart through which the blood is flowing. As a result, only the weaker, high-frequency component, i.e. the blood flow signal, is output from the high-pass filter 40. It will be understood that the greater is the velocity of the blood flow, the better will be the results of this separation based on frequency difference.

The output of the high-pass filter 40 is applied to a velocity calculating circuit 42 which calculates the velocity of the blood flow. The high-pass filter 40 and the velocity calculating circuit 42 together constitute a signal processor 44.

In the embodiment described above, the amplitude splitter splits the input signal into two output signals. The invention is not limited to this arrangement and the number of signals into which the input signal is split may instead be three or more.

Further, although the embodiment described above relates to a continuous wave type Doppler device, the invention can also be applied to a conventional pulse type Doppler device or to a secondary Doppler device of either type.

As was explained in the foregoing, in accordance with the present invention, as logarithmic amplification is carried out in a receiver, it is possible to prevent the amplifier on the reception side from being saturated by the wall signal and to effectively detect the weaker blood flow signal. Also, since the signal once converted in accordance with a logarithmic characteristic is at a later stage reconverted in accordance with an inverse logarithmic characteristic, it becomes extremely easy to separate the blood flow signal from the wall signal, enabling high-precision measurement of blood flow.

We claim:
1. An ultrasonic Doppler diagnostic device of the type which includes a means for radiating an ultrasonic wave into a living organism, a means for receiving a reflected wave from the living organism and means for detecting a frequency shift of the received wave by comparing it with a reference wave in order to detect blood flow in the living organism wherein said means for receiving comprises:
   a means for amplifying the received wave in accordance with a logarithmic amplification characteristic; said means for detecting comprising
   a plurality of inverse logarithmic converters, each of which produces an output signal having an inverse logarithmic characteristic with respect to the input thereto;
   an amplitude splitting means comprising a limiter and a subtractor, said amplitude splitting means for splitting an output signal from said means for amplifying into a low amplitude region and a high amplitude region and inputing them to said inverse logarithmic converters; and
   a weighting adding means comprising an amplifier and an adder, said weighting adding for adjusting an output signal from each of said inverse logarithmic converters to an equal level and adding them; whereby weak blood flow signals can be detected.

* * * * *